(12) United States Patent
Lin et al.

(10) Patent No.: US 6,734,686 B2
(45) Date of Patent: May 11, 2004

(54) METHOD FOR DETECTING QUANTITY VARIATION OF HIGH PURITY LIQUID CHEMICALS AND DEVICES TO CARRY OUT THE METHOD

(75) Inventors: Chi-Hui Lin, Kaohsiung (TW); Cheng-Jye Chu, Kaohsiung (TW); Pai-Mou Lee, Kaohsiung (TW); Goang-Cheng Chang, Kaohsiung (TW)

(73) Assignee: Nanmat Technology Co. Ltd., Kaohsiung (TW)

( * ) Notice: Subject to any disclaimer, the term of this patent is extended or adjusted under 35 U.S.C. 154(b) by 49 days.

(21) Appl. No.: 10/118,778

(22) Filed: Apr. 8, 2002

(65) Prior Publication Data

US 2003/0189433 A1 Oct. 9, 2003

(51) Int. Cl.[7] .......................... G01R 27/26; G01F 23/00
(52) U.S. Cl. ...................... 324/663; 324/664; 73/304 C
(58) Field of Search ................. 324/664, 661, 324/640, 643, 689, 694, 663; 73/304 C

(56) References Cited

U.S. PATENT DOCUMENTS

| | | | | |
|---|---|---|---|---|
| 5,819,582 A | * | 10/1998 | Kelly | 73/290 R |
| 5,992,231 A | * | 11/1999 | Mulder et al. | 73/304 C |
| 6,435,224 B2 | * | 8/2002 | Blatt et al. | 141/21 |
| 2002/0081232 A1 | * | 6/2002 | Lewis et al. | 422/82.02 |
| 2002/0145210 A1 | * | 10/2002 | Tompkins et al. | 261/121.1 |

* cited by examiner

Primary Examiner—N. Le
Assistant Examiner—Donald M Lair
(74) Attorney, Agent, or Firm—Kolisch Hartwell, PC

(57) ABSTRACT

This invention relates to a method for detecting quantity variation of high purity liquid chemicals by way of detecting capacitance variation to determine the liquid level of liquid chemicals. Meanwhile, the ratio of the area of the smallest electrode of the capacitor to the distance between the electrodes is adjusted to magnify the capacitance so that a very small variation can be observed clearly. This invention also discloses a device to carry out this method.

10 Claims, 3 Drawing Sheets

(i) sensing capacitance of the high purity liquid chemicals in a device, wherein the device is designed by adjusting the area of the smallest capacitor electrode and the distance between electrodes to magnify the capacitance.

↓

(ii) digitizing the capacitance.

↓

(iii) analyzing and analogizing the digital capacitance to determine the liquid level and the quantity variation of the liquid chemicals.

Fig. 1

METHOD FOR DETECTING QUANTITY VARIATION OF HIGH PURITY LIQUID CHEMICALS AND DEVICES TO CARRY OUT THE METHOD

BACKGROUND OF THE INVENTION

1. Field of the Invention

The present invention relates to a method for detecting quantity variation of high purity liquid chemicals in semi-conductor producing processes, and more particular a method that randomly measures the capacitance of the chemicals to observe tiny variations in the quantity of the chemicals. This invention also discloses devices to perform this method.

2. Description of Related Art

In processes to produce integrated circuits or deposited chips mounted on silicon wafers, a lot of chemical depositing procedures and chemical etching procedures are used in the processes. In these procedures, various high purity liquid chemicals, acting as precursors, are bubbled to become vapors or directly liquid injected. Then, the vapors are mixed with a carrier gas or liquids and then fed into a reaction chamber to be deposited on chips or wafers. The high purity liquid chemicals also can be nebulized and directly injected into the reaction room by an injector or atomizer to carry out the chemical depositing procedures. Because the thickness of the deposited layers may only be from a fraction of a nanometer to hundreds of nanometers, not much of the liquid chemical is used. Therefore, containers used to hold the liquid chemicals also have a small volume usually in the range of tens of milliliters to tens of liters.

Because conventional containers have a conventional detecting device such as a float ball or an optical device having only two or three detecting points at low, lower and empty liquid levels, knowledge of quantity variations at any time during the depositing procedure is not available. If the detecting device fails at the low liquid level, the process operator will not be aware that the liquid chemicals are very nearly depleted which may cause damage when the liquid chemicals run out and the depositing procedures are incomplete. Furthermore, conventional detecting devices have bad sensitivity. Taking the float ball for example, the float ball is not suitable used in a bubbling container that has a violently agitating liquid or with a high viscosity liquid that may stick to the float ball and damp the response of the float ball or otherwise cause false indicating signal. The optical device is not suitable to detect liquid chemicals possessing dark colors or high viscosity.

Another conventional detecting device is a platform weight scale to weigh the liquid chemicals. However, pipelines of the container are immovable, and measurement of the platform weight scale is not precise especially when the weight ratio of the liquid chemicals to the container is very small.

According to the foregoing description, processes of producing semi-conductors still have a troublesome problem with regard to the use of high purity liquid but tiny amount of chemicals. Many depositing procedures have to estimate the quantity of liquid chemical remaining in the container based on prior experience to determine when the process should be suspended to check and replenish the liquid chemicals inside the containers or replace with new containers. Therefore, the efficiency and product quality of the machines is low and the risk of missed operation is high.

The present invention has arisen to mitigate and/or obviate the disadvantages of the conventional liquid chemical detecting devices.

SUMMARY OF THE INVENTION

The main objective of the method for detecting quantity variation of high purity liquid chemicals in accordance with the present invention is to be able to detect liquid levels instantly and continuously.

Another objective of the present invention is to provide a device to carry out the method to detect the liquid levels instantly and continuously.

Further benefits and advantages of the present invention will become apparent after a careful reading of the detailed description with appropriate reference to the accompanying drawings.

BRIEF DESCRIPTION OF THE DRAWINGS

FIG. 1 is a flow chart of a method for detecting quantity variation of high quality liquid chemicals in accordance with the present invention;

DETAILED DESCRIPTION OF THE INVENTION

Figure 2:
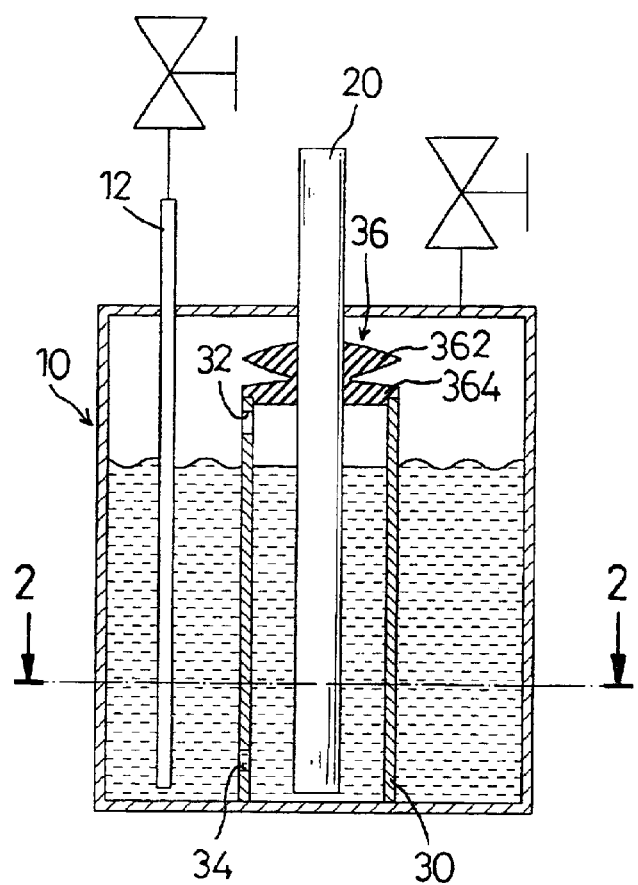
FIG. 2 is a cross sectional side plan view of a device for detecting the quantity variation of high purity liquid chemicals in accordance with the present invention.

With reference to FIG. 1, a method for detecting quantity variation of high purity liquid chemicals in accordance with the present invention comprises the following acts:

(i) sensing capacitance of the high purity liquid chemicals in a device, wherein the device is designed by adjusting the area of the smallest capacitor electrode and the distance between electrodes to magnify the capacitance being sensed;

(ii) digitizing the capacitance; and (iii) analyzing and analogizing the digital capacitance to determine the liquid level and the quantity variation of the liquid chemicals.

In act (i), a tank having a first electrode and second electrode holds the liquid chemicals inside the tank and detects the capacitance of the liquid chemicals between the electrodes. The electrodes can be tubes, plates or blocks and are made of conductive materials selected from metal such as stainless steel, aluminum, titanium, gold, platinum, or other conductive materials such as conductive glass, ceramic or polymers. The tank has to be designed in a suitable configuration to magnify the capacitance by means of following principles.

Still in act (i), changing the area of the smallest capacitor electrode and the distance between capacitor electrodes of the tank is based on the following formula:

$$C(pF) = K \times A / L$$

wherein

C: capacitance in picofarads (pF)

K: capacitance coefficient

A: area of the smallest electrode

L: distance between the two electrodes

The area of the smallest capacitor electrode is the area of the smallest electrode submerged in the liquid chemicals and is determined by the smaller area of the first electrode or the second electrode. Based on the foregoing formula, the area of the smallest electrode changes when the liquid level changes and the length between electrodes is constant. Therefore, the detected capacitance can be used to determine the liquid level. Additionally, preconceiving and presetting the ratio of A/L in maximum magnifies the capacitance to enable very small quantity variation to be easily read. When the liquid chemical in the tank is bubbling, an isolating element is mounted in the tank to prevent violent agitation from disturbing the measurement of capacitance.

In act (ii), the sensed capacitance is converted to digital data by a signal converter, and the digital data is input to a computer.

In act (iii), the computer analyzes and analogizes the digital data and analogous logic to determine the actual liquid level. The actual liquid level of the chemical in the container is displayed on a monitor driven by the computer. The actual liquid level determined by the computer can also be used to initiate audible or visual alarms or processes to replenish the liquid chemical in the container.

The method applies on bubbling liquid chemicals further comprises step of isolating part of the liquid chemicals and keeping the liquid chemicals steady when detecting the capacitance, whereby the measured capacitance of the liquid chemical is precise.

Moreover, the capacitance detecting method can be combined with other measuring techniques such as weight or volume measurement to perform a double check and ensure the precision of the quantity variation within the tank.

Figure 3:
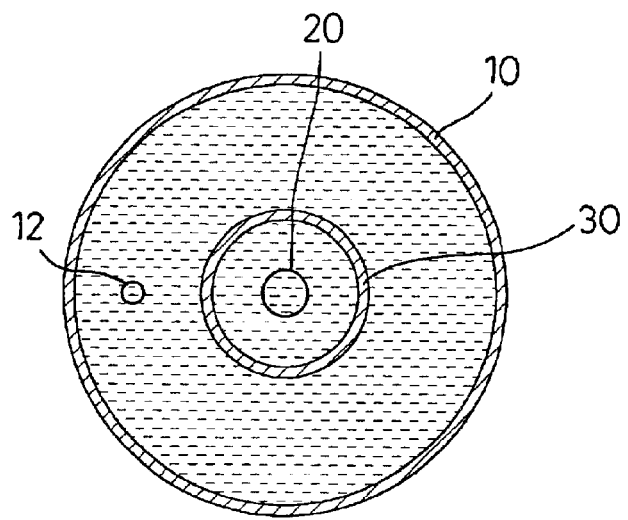
FIG. 3 is a cross-sectional top plan view of the device for detecting quantity variation of high purity liquid chemicals along line 2—2 in FIG. 1.

With reference to FIGS. 2 and 3, a capacitance detecting device used with the foregoing method in accordance with the present invention comprises an outer tank (10) and a capacitance sensor (20) insulatingly mounted inside the outer tank (10).

The outer tank (10) is a closed hollow cylinder and has a central axis, a volume of 20 ml–40L and an inner face made of conductive material, i.e. the first electrode, to measure capacitance with the sensor (20). An inlet pipe (12) is mounted in the tank and almost reaches the bottom of the tank so the carrier gas mixes well with the liquid chemical.

The sensor (20) is the second electrode and is mounted along the central axis of the outer tank (10) in an insulating situation to detect the capacitance of the liquid chemical between the outer tank (10) and the sensor (20).

However, when the liquid is bubbled, the liquid chemicals are agitated and are not homogenous so the sensed capacitance fluctuates. To prevent or mitigate errors caused from liquid agitation, a baffle (30) is mounted around the sensor (20) between the outer tank (10) and the sensor (20) to isolate the agitating liquid chemicals. The baffle (30) is cylindrical, has a top and a bottom and is also made of conductive material to replace the outer tank (10) as the first electrode. At least one first through hole (32) is defined through the baffle (30) near the top as a vacuum breaker, and at least one second through hole (34) is defined through the baffle (30) near the bottom to allow the liquid chemicals to freely flow through the baffle (30). Whereby, the liquid level inside and outside the baffle (30) are the same and the liquid agitation is isolated from the inside of the baffle (30) so the sensed capacitance is precise.

Moreover, to prevent a conductive liquid membrane from forming between electrically shorting the baffle (30) and the sensor (20), a nonconductor (36) covers the top of the baffle (30) to isolate the baffle (30) and the sensor (20). The nonconductor (36) is divided into an upper guide (362) and a lower cap (364). The upper guide (362) is oval and lays on top of the lower cap (364). Thus when liquid wets the upper guide (362), the liquid flows along the curved surface of the upper guide (362) and drips from the edges of the guide (362). Therefore, a liquid membrane cannot form to electrically short the first and the second electrodes. The lower cap (364) also has a curved bulged surface to shed the liquid chemicals.

Figure 4:
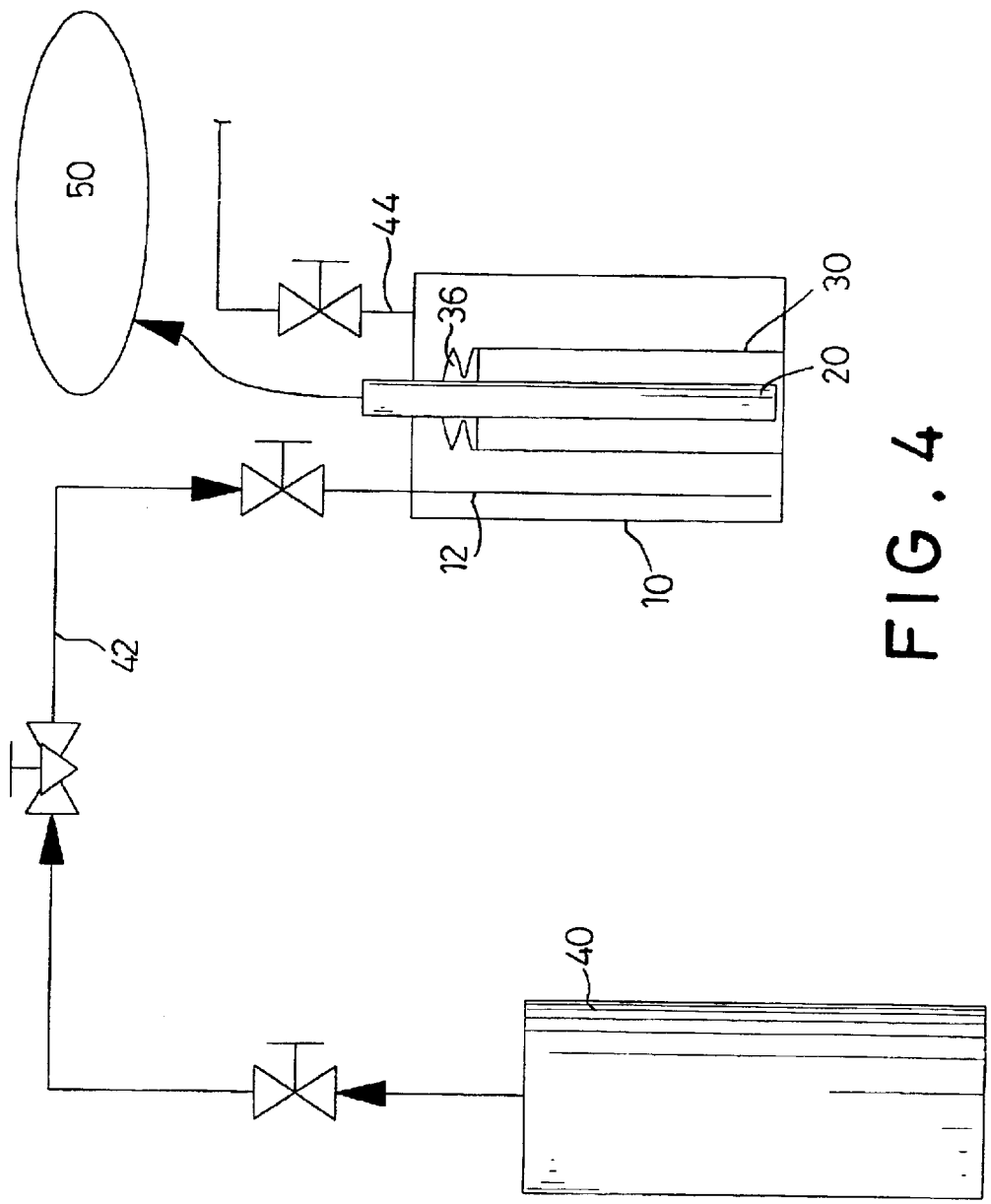
FIG. 4 is an operational piping diagram of the device in FIG. 1, wherein the device interfaces with other equipment.

With reference to FIG. 4, a pressure cylinder (40) is connected to the inlet pipe (12) to supply carrier gas to the outer tank (10). In the outer tank (10), the carrier gas reacts with the liquid chemicals to form a process gas. After the carrier gas reacts with the liquid chemicals, the process gas is discharged through an outlet pipe (44) to a reaction chamber (not shown) to compose a depositing layer on a substrate or a wafer. During the depositing procedure, the sensor (20) instantly transmits the sensed capacitance signal to an analog to digital converter (not shown) where the sensor (20) signal is converted to digital signal, and the digitized capacitance signal is further transmitted to a computer calculating system (50). The digital signal is analyzed and analogized in the computer calculating system (50) to determine the liquid level.

Although the invention has been explained in relation to its preferred embodiment, it is to be understood that many other possible modifications and variations can be made without departing from the spirit and scope of the invention as hereinafter claimed.

What is claimed is:

1. A method for detecting quantity variation of high purity liquid chemicals, the method comprises the following acts of:
   (i) sensing capacitance of the high purity liquid chemicals in a device having a smallest capacitor electrode and an outer electrode, wherein the device is designed by adjusting the area of the smallest capacitor electrode and the distance between the smallest capacitor electrode and the outer electrode to magnify the capacitance to be sensed;
   (ii) digitizing the capacitance; and
   (iii) analyzing and analogizing the digital capacitance to determine the liquid level and the quantity variation of the liquid chemicals.

2. The method for detecting quantity variation of high purity liquid chemicals as claimed in claim 1, wherein the method adapted to apply on bubbling liquid chemicals further comprises:
   isolating part of the liquid chemicals and keeping the liquid chemicals steady when detecting the capacitance, whereby the measured capacitance of the liquid chemical is precise.

3. The method for detecting quantity variation of high purity liquid chemicals as claimed in claim 2, wherein the method further comprises weight measurement and volume measurement to double check the quantity variation of the liquid chemical and simultaneously show the capacitance of the liquid chemicals in a monitor.

4. The method for detecting quantity variation of high purity liquid chemicals as claimed in claim 1, wherein the method further comprises weight measurement and volume measurement to double check the quantity variation of the liquid chemical and simultaneously show the capacitance of the liquid chemicals in a monitor.

5. A device adapted to carry out the method for detecting quantity variation in claim 1, the device comprising:

an outer tank (10) being a hollow cylinder with a central axis and a first electrode; and a sensor (20) mounted on the central axis of the outer tank (10) and being a second electrode;

wherein the capacitance of the liquid chemicals between the outer tank (10) and the sensor (20) is measured.

6. The device for detecting quantity variation as claimed in claim 5, wherein the device is adapted to be used with bubbling liquids of depositing procedures and further comprises:

an inlet pipe (12) inserting into the outer tank (10) to inject a carrier gas;

a baffle (30) being a hollow cylinder, having a top and a bottom and mounted around the sensor (20) between the outer tank (10) and the sensor (20) to isolate the agitating liquid chemicals and to replace the outer tank (10) as the first electrode;

at least one first through hole (32) defined in the baffle (30) near the top as a vacuum breaker; and at least one second hole (34) defined in the baffle (30) near the bottom so the liquid chemicals can flow through the baffle (30).

7. The device for detecting quantity variation as claimed in claim 6, in which a nonconductor (36) covers the top of the baffle (30) to isolate the baffle (30) and the sensor (20) and to prevent an electrical short between the baffle (30) and the sensor (20).

8. The device for detecting quantity variation as claimed in claim 7, wherein the nonconductor (36) is divided into an upper guide (362) and a lower cap (364);

wherein the upper guide (362) is oval and lays on top of the lower cap (364); the lower cap (364) covers the top of the baffle (30) and has a curved bulged surface to shed the liquid chemicals.

9. The device for detecting quantity variation as claimed in claim 8, the first and the second electrodes being made of conductive materials selected from metal such as stainless steel, aluminum, titanium, gold and platinum, or other conductive materials such as conductive glass, ceramic and polymers.

10. The device for detecting quantity variation as claimed in claim 5, the first and the second electrodes being made of conductive materials selected from metal such as stainless steel, aluminum, titanium, gold and platinum, or oilier conductive materials such as conductive glass, ceramic and polymers.

* * * * *